US011630056B1

(12) United States Patent
Harb et al.

(10) Patent No.: US 11,630,056 B1
(45) Date of Patent: Apr. 18, 2023

(54) VACUUM AIRFLOW FILTERING FOR BIOLOGICAL SENSING

(71) Applicant: RingIR, Inc., Albuquerque, NM (US)

(72) Inventors: Charles Charbel Harb, Albuquerque, NM (US); Ruwini Dinushika Rajapaksha, Albuquerque, NM (US); John Michael Roberts, Tijeras, NM (US)

(73) Assignee: RINGIR, INC., Albuquerque, NM (US)

( * ) Notice: Subject to any disclaimer, the term of this patent is extended or adjusted under 35 U.S.C. 154(b) by 0 days.

(21) Appl. No.: 17/539,140

(22) Filed: Nov. 30, 2021

(51) Int. Cl.

| | |
|---|---|
| ***G01N 21/31*** | (2006.01) |
| ***G01N 21/94*** | (2006.01) |
| ***G01N 33/497*** | (2006.01) |
| ***B01D 46/00*** | (2022.01) |

(52) U.S. Cl.
CPC ......... *G01N 21/31* (2013.01); *B01D 46/0028* (2013.01); *B01D 46/0049* (2013.01); *G01N 21/94* (2013.01); *G01N 33/497* (2013.01); *B01D 2279/65* (2013.01); *G01N 2033/4975* (2013.01)

(58) Field of Classification Search
CPC ...... G01N 21/31; G01N 21/94; G01N 33/497; G01N 2033/4975; B01D 46/0028; B01D 46/0049; B01D 2279/65
See application file for complete search history.

(56) References Cited

U.S. PATENT DOCUMENTS

2021/0302346 A1* 9/2021 Tobjork ............... G01N 33/007

OTHER PUBLICATIONS

Glen et al (RingIR AG-4000 Testing, Sandia National Laboratories, Jan. 2021, pp. 1-15.) (Year: 2021).*

Rajapaksha et al "A Rapid and Sensitive Chemical Screening Method for E-Cigarette Aerosols Based on Runtime Cavity Ringdown Spectroscopy" Environmental Science & Technology 2021 55 (12), 8090-8096. (Year: 2021).*

Boyson et al, Real-Time Multiplexed Digital Cavity-Enhanced Spectroscopy. Opt. Lett. 2015, 40 (19), 4560 (Year: 2015).*

* cited by examiner

*Primary Examiner* — Dennis White
(74) *Attorney, Agent, or Firm* — Dickinson Wright PLLC

(57) ABSTRACT

Systems for biological sensing that include, in one implementation, a sensor, a filter, a pump, and a flow channel. The sensor is configured to test a gas sample. The sensor includes an optical cavity. The filter is configured to filter the gas sample. The flow channel is formed by at least the optical cavity, the filter, and the pump. The pump is configured to generate a negative pressure differential inside the flow channel.

17 Claims, 4 Drawing Sheets

Gas in
2
16
4
Sensor
12
Optical Cavity
10
14
18
8
Pump
20
6
Filter
Gas Out

VACUUM AIRFLOW FILTERING FOR BIOLOGICAL SENSING

BACKGROUND

Detecting infected patients is one important part of mitigating disease transmission during a pandemic. To this end, a spectrometer can be used to detect infected patients. For example, a spectrometer that performs cavity ring-down spectroscopy (CRDS) can be used for human breath analysis to diagnose SARS-CoV-2 (i.e., COVID-19). CRDS measures changes in the rate of decay of light captured in an optical cavity and relates the change to optical loss along the length of the optical cavity.

SUMMARY

To prevent pathogen exposure to subsequent users of a spectrometer, a filter can be installed in the exhaust of an optical cavity in the spectrometer to capture infectious particles. While the filter may capture nearly all the infectious particles that pass through it, the spectrometer can still expel infectious particles through leaks in its flow channel. Accordingly, the present disclosure provides systems for biological sensing that, among other things, generate negative pressure inside their flow channels to ensure any leaks will pull in clean outside air, rather than expel potentially dangerous sample gas while in operation.

For example, the present disclosure provide a system for biological sensing that includes, in one implementation, a sensor, a filter, a pump, and a flow channel. The sensor is configured to test a gas sample. The sensor includes an optical cavity. The filter is configured to filter the gas sample. The flow channel is formed by at least the optical cavity, the filter, and the pump. The pump is configured to generate a negative pressure differential inside the flow channel.

The present disclosure also provides a system for biological sensing that includes, in one implementation, a first air conduit, a sensor, a second air conduit, a filter, a third air conduit, a pump, a fourth air conduit, and a flow channel. The first air conduit is configured to receive an air sample. The sensor is configured to test the air sample. The sensor includes an optical cavity that is coupled to the first air conduit. The second air conduit is coupled to the optical cavity. The filter is configured to filter the air sample. The filter is coupled to the second air conduit. The third air conduit is coupled to the filter. The pump is coupled to the third air conduit. The fourth air conduit is configured to release the air sample. The fourth air conduit is coupled to the pump. The flow channel is formed by at least the first air conduit, the optical cavity, the second air conduit, the filter, the third air conduit, the pump, and the fourth air conduit. The pump is configured to generate a negative pressure differential inside the flow channel.

The present disclosure further provides a system for biological sensing that includes, in one implementation, a first air conduit, a sensor, a second air conduit, a pump, a third air conduit, and a filter. The first air conduit is configured to receive an air sample. The sensor is configured to test the air sample. The sensor includes an optical cavity that is coupled to the first air conduit. The second air conduit is coupled to the optical cavity. The pump is coupled to the second air conduit. The third air conduit is coupled to the pump. The filter is configured to filter and release the air sample. The filter is coupled to the third air conduit. The flow channel is formed by at least the first air conduit, the optical cavity, the second air conduit, the pump, the third air conduit, and the filter. The pump is configured to generate a negative pressure differential inside the flow channel.

Other technical features may be readily apparent to one skilled in the art from the following figures, descriptions, and claims.

BRIEF DESCRIPTION OF THE DRAWINGS

For a more complete understanding of the present disclosure and its advantages, reference is now made to the following description, taken in conjunction with the accompanying drawings. It is emphasized that, according to common practice, the various features of the drawings are not necessarily to-scale. On the contrary, the dimensions of the various features may be—and typically are—arbitrarily expanded or reduced for the purpose of clarity.

NOTATION AND NOMENCLATURE

Figure 1:
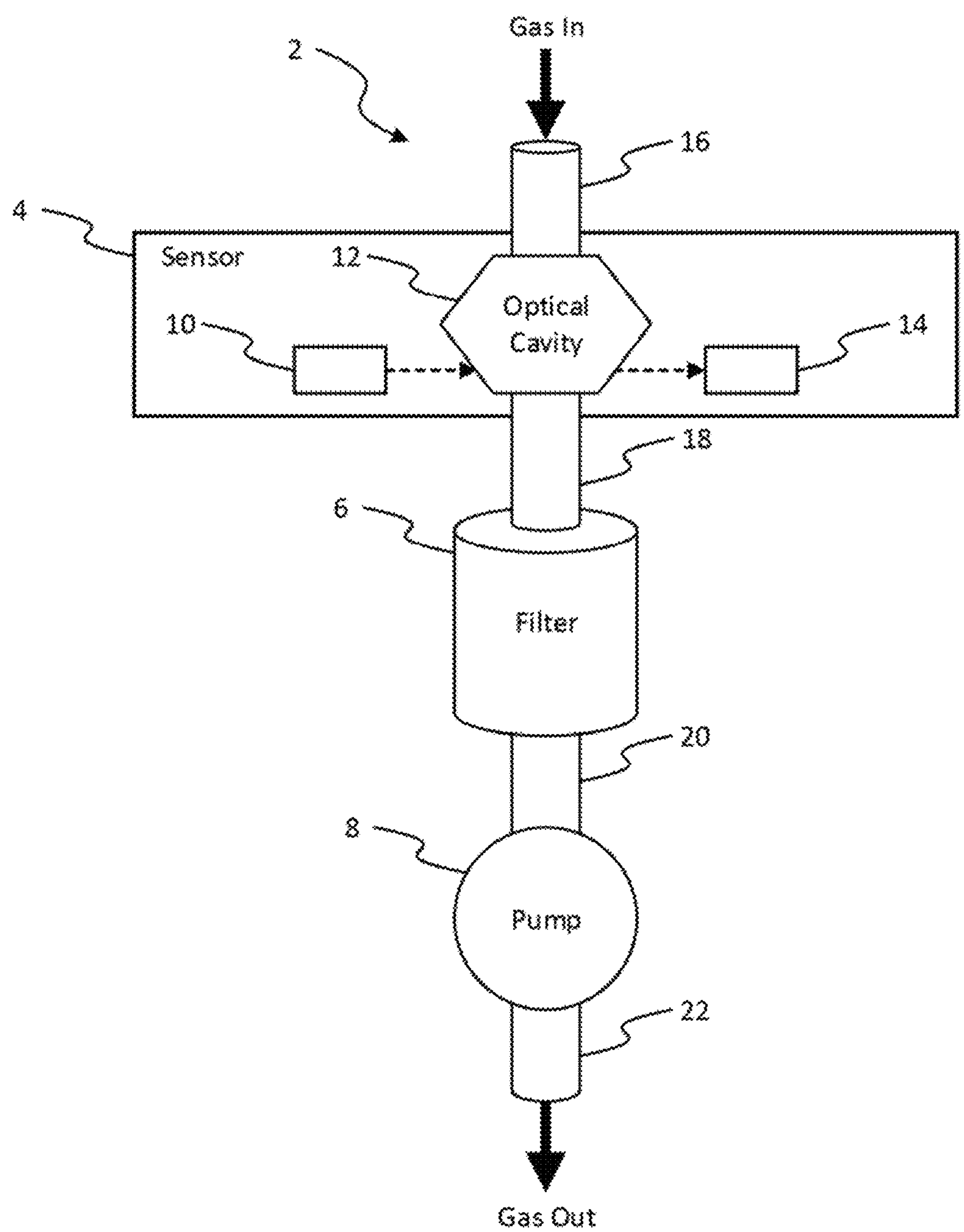
FIG. 1 is a block diagram of an example of a system for biological sensing, in accordance with some implementations of the present disclosure.

Various terms are used to refer to particular system components. A particular component may be referred to commercially or otherwise by different names. Further, a particular component (or the same or similar component) may be referred to commercially or otherwise by different names. Consistent with this, nothing in the present disclosure shall be deemed to distinguish between components that differ only in name but not in function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection, or through an indirect connection via other devices and connections.

The terminology used herein is for the purpose of describing particular example implementations only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example implementations. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "up," "upper," "top," "bottom," "down," "inside," "outside," "contained within," "superimposing upon," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

"Real-time" may refer to less than or equal to 2 seconds. "Near real-time" may refer to any interaction of a sufficiently short time to enable two individuals to engage in a dialogue via such user interface, and will generally be less than 10 seconds (or any suitable proximate difference between two different times) but greater than 2 seconds.

DETAILED DESCRIPTION

The following discussion is directed to various implementations of the present disclosure. Although one or more of these implementations may be preferred, the implementations disclosed should not be interpreted, or otherwise used, as limiting the scope of the present disclosure, including the claims. In addition, one skilled in the art will understand that the following description has broad application, and the discussion of any implementation is meant only to be exemplary of that implementation, and not intended to intimate that the scope of the disclosure, including the claims, is limited to that implementation.

FIG. 1 is a block diagram of an example of a system 2 for biological sensing (e.g., a spectrometer). The system 2 illustrated in FIG. 1 includes a sensor 4, a filter 6, and a pump 8. The system 2 may include fewer, additional, or different components in different configurations than the system 2 illustrated in FIG. 1. For example, in some implementations, the system 2 may include multiple sensors. The sensor 4 illustrated in FIG. 1 (e.g., a spectrometer) includes a light emitter 10, an optical cavity 12, and a light detector 14. As illustrated in FIG. 1, a gas sample flows through the optical cavity 12. The light emitter 10 emits light into the optical cavity 12. For example, the light emitter 10 may include a quantum cascade laser that emits mid-infrared light (e.g., between 6 and 12 microns). The light detector 14 detects the intensity of light within the optical cavity 12. When the light is in resonance, the intensity builds up in the optical cavity 12 due to constructive interference. The light emitter 10 is then turned off in order to allow the measurement of the exponentially decaying light intensity leaking from the optical cavity 12. During this decay, light is reflected back and forth many times within the optical cavity 12. The exponentially decaying light intensity is due to, among other things, scattering caused by the gas sample (also referred to herein as an air sample) flowing through the optical cavity 12. The composition of the gas sample flowing through the optical cavity 12 can be determined by measuring the decaying exponential. For example, the mole fractions (down to, e.g., the parts per trillion level) of the gas sample flowing through the optical cavity 12 can be determined by measuring the decaying exponential.

The gas sample is expelled from the system 2 after passing through the optical cavity 12. As the gas sample may contain infectious particles, the filter 6 captures most of the infectious particles in the gas sample. In this manner, the filter 6 ensures users are not exposed to any potential biohazards in the gas sample. Further, the filter 6 ensures the output is nominally safe and allows for testing of biohazards with standard medical personal protective equipment (PPE) outside of a biosafety cabinet. In some implementations, the filter 6 includes a high-efficiency particulate air (HEPA) filter. HEPA filters may be certified to filter approximately 99.97% of pathogens in the gas sample.

The system 2 illustrated in FIG. 1 also includes a plurality of air conduits 16, 18, 20, and 22. Air conduit 16 (an example of a "first air conduit") receives an air sample and is coupled to the optical cavity 12. The optical cavity 12 illustrated in FIG. 1 is coupled to the filter 6 via air conduit 18 (an example of a "second air conduit"). The filter 6 illustrated in FIG. 1 is coupled to the pump 8 via air conduit 20 (an example of a "third air conduit"). Air conduit 22 (an example of a "fourth air conduit") releases the air sample.

Portions of the gas sample may leak out of the system 2 before being filtered by the filter 6. For example, portions of the gas sample may leak through microscopic openings present near, e.g., couplers included in the system 2. Thus, some infectious particles in the gas sample may also leak out of the system 2. To prevent leaks, the pump 8 is configured to generate a negative pressure differential inside a flow channel formed by, e.g., the optical cavity 12, the filter 6, the pump 8, and the plurality of air conduits 16, 18, 20, and 22. The lower cavity pressure ensures any microscopic leak will pull in clean outside air, rather than expel potentially dangerous sample gas while the system 2 is in operation. The pump 8 (e.g., a vacuum or air pump) pulls the gas sample through the flow channel. In this manner, the entire gas sample travels through the filter 6 and almost all the infectious particles in the gas sample are captured in the filter 6. In some implementations, the pump 8 includes a swing piston gas pump (e.g., the NPK04KVDC-B Swing Piston Vacuum Pump from KNF which provides a 3.3 liter per minute maximum flow rate). The system 2 moves a high throughput of gas through the flow channel. This is different for other designs that use only a small portion of gas from a sample bag or designs that use gas chromatography.

Figure 2:
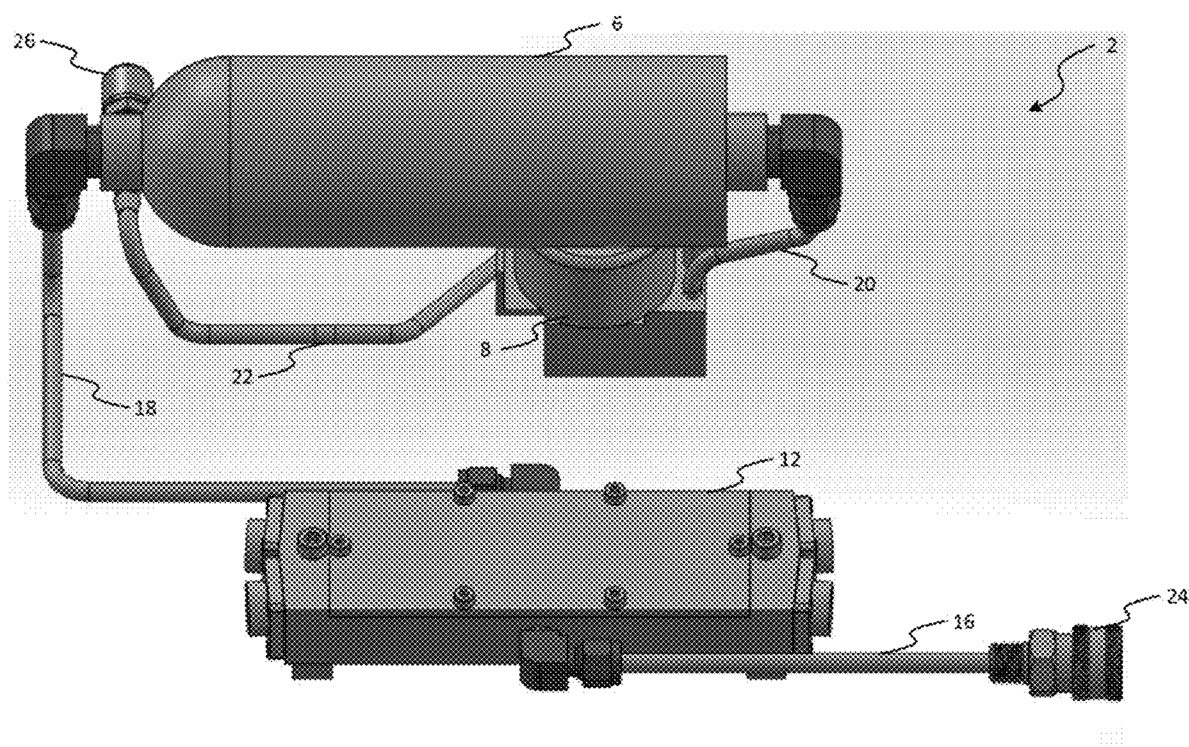
FIG. 2 is a perspective view of the system of FIG. 1, in accordance with some implementations of the present disclosure.
Figure 3:
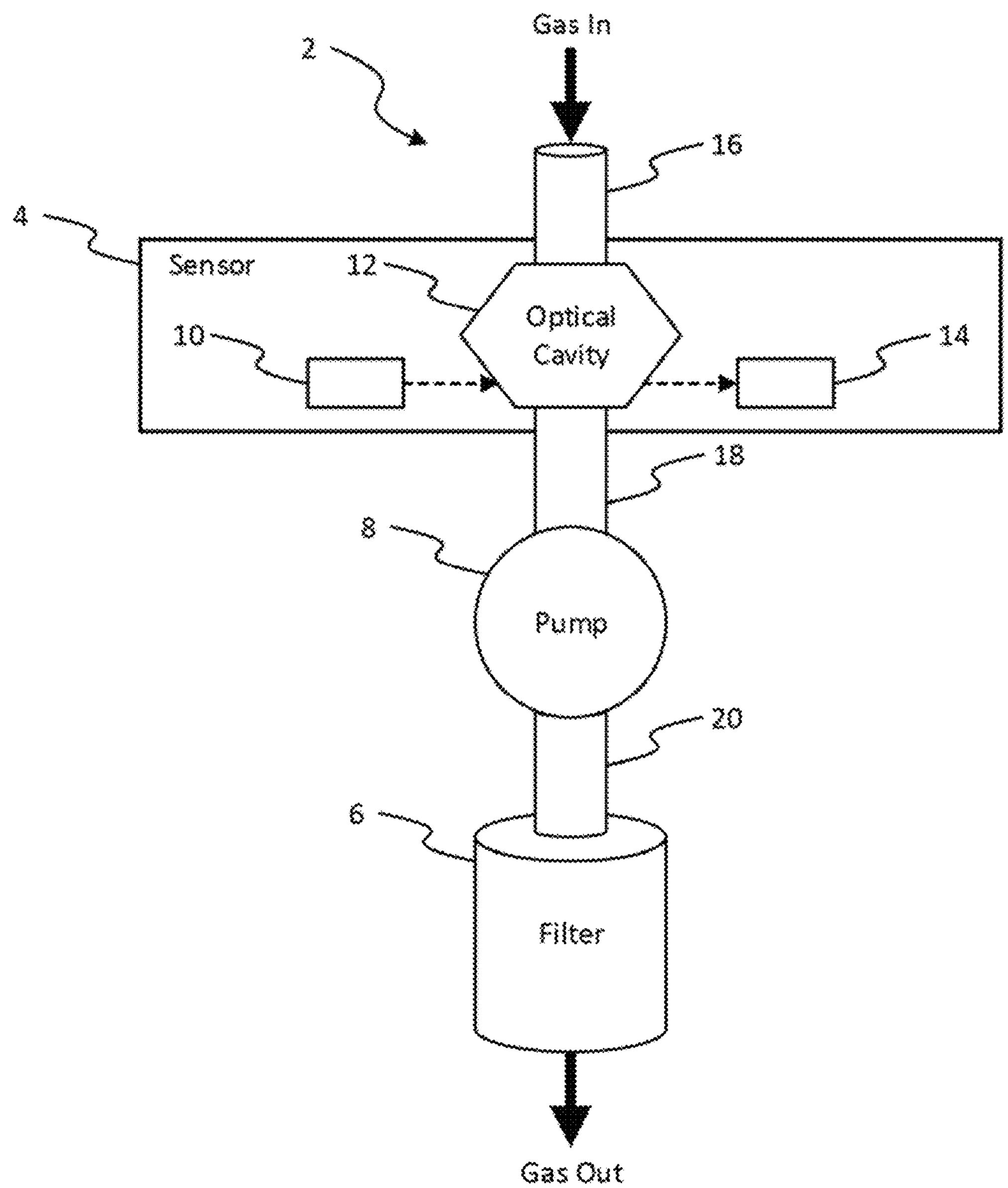
FIG. 3 is a block diagram of an example of a system for biological sensing that includes a different arrangement of components than the system of FIG. 1, in accordance with some implementations of the present disclosure.
Figure 4:
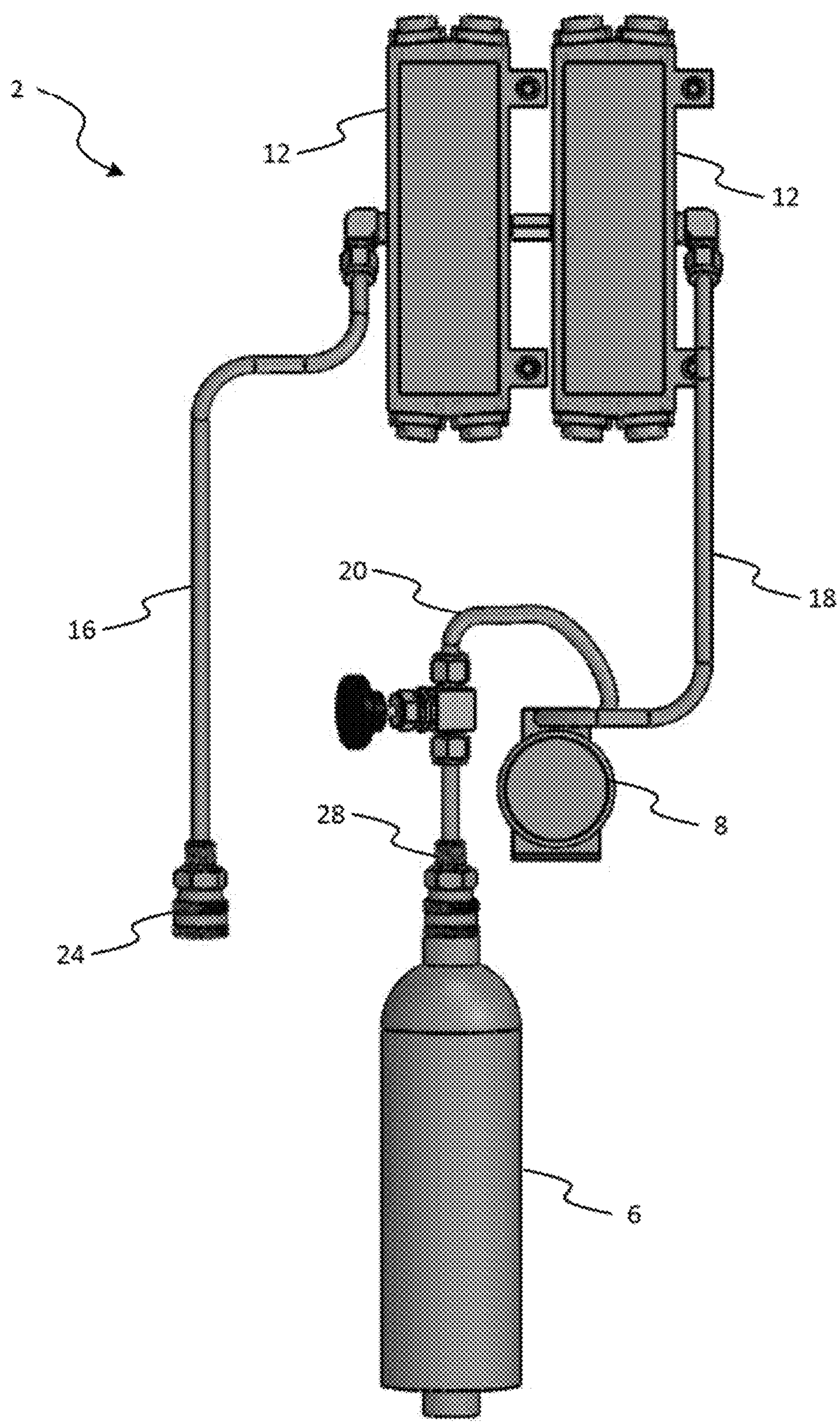
FIG. 4 is a perspective view of an example of a system for biological sensing that includes two sensors, in accordance with some implementations, in accordance with some implementations of the present disclosure.

In some implementations, the filter 6 is positioned on the flow channel between the optical cavity 12 and the pump 8, as illustrated in FIG. 1. Further, FIG. 2 is a perspective view of an example of the system 2 for biological filtering in which the filter 6 is positioned on the flow channel between the optical cavity 12 and the pump 8. In alternate implementations, the pump 8 may be positioned on the flow channel between the optical cavity 12 and the filter 6, as illustrated in FIG. 3. Further, FIG. 4 is a perspective view of an example of the system 2 in which the pump 8 is positioned on the flow channel between the optical cavity 12 and the filter 6. In the system 2 illustrated in FIGS. 1 and 2, air conduit 22 releases the gas sample. In the system 2 illustrated in FIGS. 3 and 4, the filter 6 releases the gas sample.

In some implementations, a tube fitting may be positioned on the input side of the flow channel. For example, in FIGS. 2 and 4, a Swagelok fitting 24 (an example of a "first tube fitting") is coupled to air conduit 16. During breath sample testing, a breath bag may be attached to Swagelok fitting 24 while the pump 8 is operating to ensure sample introduction is carried out in negative pressure. In some implementations, a tube fitting may be positioned on the outside side of the flow channel. For example, in FIG. 2, a Swagelok fitting 26 (an example of a "second tube fitting") is coupled to air conduit 22. Alternatively, or in addition, a tube fitting may be positioned between the pump 8 and the filter 6. For example, in FIG. 4, a Swagelok fitting 28 (another example of a "second tube fitting") is positioned between air conduit 20 and the filter 6.

The gas sample (or air sample) may include a breath sample from a patient (e.g., contained within a breath bag). Alternatively, or in addition, the gas sample (or air sample) includes other types of samples (e.g., an ambient indoor air sample, an ambient outdoor air sample, and the like).

In some implementations, the system 2 includes a single sensor 4. For example, the system 2 illustrated in FIG. 1 includes one sensor 4 (and thus one optical cavity 12). In alternate implementations, the system 2 includes multiple sensors (e.g., to scan at different optical bandwidths). For example, the system 2 illustrated in FIG. 4 includes two sensors 4 (and thus two optical cavities 12). The optical cavities 12 of different sensors 4 may be coupled to each other. For example, in FIG. 4, the output of one of the optical cavities 12 is coupled to the input of the other optical cavity 12. In some implementations, the system 2 includes a single sensor 4 with an optical bandwidth between, e.g., approximately 6.73 microns and 11 microns. In alternate implementations, the system 2 includes a first optical sensor 4 with an optical bandwidth between, e.g., approximately 6.73 microns and 8.65 microns, and a second optical sensor 4 with an optical bandwidth between, e.g., approximately 8.65 microns and 11 microns.

In some implementations, the sample gas is introduced into the flow channel from a sample bag. In some implementations, the optical cavity 12 is sealed with O-rings and vacuum grease, and all other possible leak points are coated with a vacuum epoxy sealant to create a pneumatic loop which ensures no leakage until the gas exits the system 2. In some implementations, all pneumatic fittings in the system 2 are leak-proof and swaged onto stainless steel tubing, ensuring the gas output can be plumbed directly, e.g., into an appropriate fume or biosafety hood. In some implementations, the flow channel is purged with room air in between each sample and tested for residuals from previous sample by capturing background spectrum. This ensures the cavities are clean and no remaining aerosols from previous samples are present.

Consistent with the above disclosure, the examples of systems and methods enumerated in the following clauses are specifically contemplated and are intended as a non-limiting set of examples.

Clause 1. A system for biological sensing, the system comprising:

a sensor configured to test a gas sample, wherein the sensor including an optical cavity;

a filter configured to filter the gas sample;

a pump; and a flow channel formed by at least the optical cavity, the filter, and the pump, wherein the pump is configured to generate a negative pressure differential inside the flow channel.

Clause 2. The system of any clause herein, wherein the filter is positioned on the flow channel between the optical cavity and the pump.

Clause 3. The system of any clause herein, further comprising:

a first tube fitting positioned on an input side of the flow channel; and a second tube fitting positioned on an output side of the flow channel.

Clause 4. The system of any clause herein, wherein the pump is positioned on the flow channel between the optical cavity and the filter.

Clause 5. The system of any clause herein, further comprising:

a first tube fitting positioned on an input side of the flow channel; and a second tube fitting positioned between the pump and the filter.

Clause 6. The system of any clause herein, wherein the system further comprises a second sensor configured to test the gas sample, wherein the second sensor including a second optical cavity, and wherein the flow channel is further formed by the second optical cavity.

Clause 7. The system of any clause herein, wherein the sensor is configured for cavity ring-down spectroscopy.

Clause 8. The system of any clause herein, wherein the filter includes a high-efficiency particulate air (HEPA) filter.

Clause 9. The system of any clause herein, wherein the pump is further configured to pull the gas sample through the flow channel.

Clause 10. A system for biological sensing, the system comprising:

a first air conduit configured to receive an air sample;

a sensor configured to test the air sample, wherein the sensor including an optical cavity coupled to the first air conduit;

a second air conduit coupled to the optical cavity;

a filter configured to filter the air sample, wherein the filter is coupled to the second air conduit;

a third air conduit coupled to the filter;

a pump coupled to the third air conduit;

a fourth air conduit configured to release the air sample, wherein the fourth air conduit is coupled to the pump; and a flow channel formed by at least the first air conduit, the optical cavity, the second air conduit, the filter, the third air conduit, the pump, and the fourth air conduit, wherein the pump configured to generate a negative pressure differential inside the flow channel.

Clause 11. The system of any clause herein, further comprising:

a first tube fitting coupled to the first air conduit; and a second tube coupled to the fourth air conduit.

Clause 12. The system of any clause herein, wherein the sensor is configured for cavity ring-down spectroscopy.

Clause 13. The system of any clause herein, wherein the filter includes a high-efficiency particulate air (HEPA) filter.

Clause 14. The system of any clause herein, wherein the pump is further configured to pull the air sample through the flow channel.

Clause 15. A system for biological sensing, the system comprising:

a first air conduit configured to receive an air sample;

a sensor configured to test the air sample, wherein the sensor including an optical cavity coupled to the first air conduit;

a second air conduit coupled to the optical cavity;

a pump coupled to the second air conduit;

a third air conduit coupled to the pump;

a filter configured to filter and release the air sample, wherein the filter is coupled to the third air conduit; and a flow channel formed by at least the first air conduit, the optical cavity, the second air conduit, the pump, the third air conduit, and the filter, wherein the pump is configured to generate a negative pressure differential inside the flow channel.

Clause 16. The system of any clause herein, further comprising:

a first tube fitting coupled to the first air conduit; and a second tube fitting coupled between the pump and the filter.

Clause 17. The system of any clause herein, wherein the system further comprises a second sensor configured to test the air sample, wherein the second sensor including a second optical cavity, and wherein the flow channel is further formed by the second optical cavity.

Clause 18. The system of any clause herein, wherein the sensor is configured for cavity ring-down spectroscopy.

Clause 19. The system of any clause herein, wherein the filter includes a high-efficiency particulate air (HEPA) filter.

Clause 20. The system of any clause herein, wherein the pump is further configured to pull the air sample through the flow channel.

No part of the description in this application should be read as implying that any particular element, step, or function is an essential element that must be included in the claim scope. The scope of patented subject matter is defined only by the claims. Moreover, none of the claims is intended to invoke 25 U.S.C. § 104(f) unless the exact words "means for" are followed by a participle.

The foregoing description, for purposes of explanation, use specific nomenclature to provide a thorough understanding of the described embodiments. However, it should be apparent to one skilled in the art that the specific details are not required to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present disclosure. Once the above disclosure is fully appreciated, numerous variations and modifications will become apparent to those skilled in the art. It is intended that the following claims be interpreted to embrace all such variations and modifications.

What is claimed is:

1. A system for biological sensing, the system comprising:

a sensor configured to test a gas sample, wherein the sensor including an optical cavity, wherein the sensor is configured for cavity ring-down spectroscopy;

a filter configured to filter and release the gas sample;

a pump; and a flow channel formed by at least the optical cavity, the filter, and the pump, wherein the pump is configured to generate a negative pressure differential inside the flow channel, and wherein the filter is positioned at an end of the flow channel.

2. The system of claim 1, wherein the pump is positioned on the flow channel between the optical cavity and the filter.

3. The system of claim 2, further comprising:

a first tube fitting positioned on an input side of the flow channel; and a second tube fitting positioned between the pump and the filter.

4. The system of claim 1, wherein the sensor is a first sensor, wherein the system further comprises a second sensor configured to test the gas sample, wherein the second sensor including a second optical cavity, and wherein the flow channel is further formed by the second optical cavity.

5. The system of claim 4, wherein the first sensor has a first optical bandwidth, and wherein the second sensor has a second optical bandwidth different than the first optical bandwidth.

6. The system of claim 5, wherein the first optical bandwidth is between 6.73 microns and 8.65 microns, and wherein the second optical bandwidth is between 8.65 microns and 11 microns.

7. The system of claim 1, wherein the filter includes a high-efficiency particulate air (HEPA) filter.

8. The system of claim 1, wherein the pump is further configured to pull the gas sample through the flow channel.

9. The system of claim 1, wherein the sensor further includes a quantum cascade laser and a light detector.

10. A system for biological sensing, the system comprising:

a first air conduit configured to receive an air sample;

a sensor configured to test the air sample, wherein the sensor including an optical cavity coupled to the first air conduit, wherein the sensor is configured for cavity-ring down spectroscopy;

a second air conduit coupled to the optical cavity;

a pump coupled to the second air conduit;

a third air conduit coupled to the pump;

a filter configured to filter and release the air sample, wherein the filter is coupled to the third air conduit; and a flow channel formed by at least the first air conduit, the optical cavity, the second air conduit, the pump, the third air conduit, and the filter, wherein the pump is configured to generate a negative pressure differential inside the flow channel, and wherein the filter is positioned at an end of the flow channel.

11. The system of claim 10, further comprising:

a first tube fitting coupled to the first air conduit; and a second tube fitting coupled between the pump and the filter.

12. The system of claim 10, wherein the sensor is a first sensor, wherein the system further comprises a second sensor configured to test the air sample, wherein the second sensor including a second optical cavity, and wherein the flow channel is further formed by the second optical cavity.

13. The system of claim 12, wherein the first sensor has a first optical bandwidth, and wherein the second sensor has a second optical bandwidth different than the first optical bandwidth.

14. The system of claim 13, wherein the first optical bandwidth is between 6.73 microns and 8.65 microns, and wherein the second optical bandwidth is between 8.65 microns and 11 microns.

15. The system of claim 10, wherein the filter includes a high-efficiency particulate air (HEPA) filter.

16. The system of claim 10, wherein the pump is further configured to pull the air sample through the flow channel.

17. The system of claim 10, wherein the sensor further includes a quantum cascade laser and a light detector.

* * * * *